(12) United States Patent
Ellis et al.

(10) Patent No.: US 7,842,012 B2
(45) Date of Patent: *Nov. 30, 2010

(54) GUIDEWIRE WITH CHEMICAL SENSING CAPABILITIES

(75) Inventors: Jeffrey T. Ellis, San Francisco, CA (US); Robert D. Ainsworth, Scotts Valley, CA (US); Deborah L. Kilpatrick, Mountain View, CA (US); Alex Q. Tilson, Burlingame, CA (US); Bridget A. Hurley, San Francisco, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 267 days.

This patent is subject to a terminal disclaimer.

(21) Appl. No.: 11/346,771

(22) Filed: Feb. 3, 2006

(65) Prior Publication Data
US 2006/0129041 A1 Jun. 15, 2006

Related U.S. Application Data

(63) Continuation of application No. 09/967,186, filed on Sep. 28, 2001, now Pat. No. 7,025,734.

(51) Int. Cl.
*A61M 5/178* (2006.01)
*A61M 25/00* (2006.01)

(52) U.S. Cl. ................... 604/164.13; 600/585
(58) Field of Classification Search ........ 600/345, 600/433, 434, 435, 585; 604/158, 164.13, 604/170.01, 171
See application file for complete search history.

(56) References Cited

U.S. PATENT DOCUMENTS

| 4,801,538 | A | | 1/1989 | Hanada et al. |
| 4,966,148 | A | | 10/1990 | Millar |
| 5,124,130 | A | | 6/1992 | Costello et al. |
| 5,176,882 | A | | 1/1993 | Gray et al. |
| 5,345,932 | A | | 9/1994 | Yafuso et al. |
| 5,434,085 | A | | 7/1995 | Capomacchia et al. |
| 5,496,294 | A | * | 3/1996 | Hergenrother et al. ...... 604/524 |
| 5,582,170 | A | | 12/1996 | Soller |
| 5,603,820 | A | | 2/1997 | Malinski et al. |
| 5,617,870 | A | | 4/1997 | Hastings et al. |
| 5,776,100 | A | | 7/1998 | Forman |

(Continued)

FOREIGN PATENT DOCUMENTS

WO 94/02845 3/1994

(Continued)

OTHER PUBLICATIONS

"wire." Dictionary.com Unabridged (v 1.1). Random House, Inc. Apr. 21, 2008. <Dictionary.com http://dictionary.reference.com/browse/wire>.*

(Continued)

*Primary Examiner*—Max Hindenburg
*Assistant Examiner*—Jonathan M Foreman
(74) *Attorney, Agent, or Firm*—Squire, Sanders & Dempsey L.L.P.

(57) ABSTRACT

A guidewire with a sensor which can detect NO and/or superoxide levels is disclosed. This invention can be useful for in vivo analysis of vascular health.

24 Claims, 6 Drawing Sheets

U.S. PATENT DOCUMENTS

| | | | |
|---|---|---|---|
| 5,788,647 | A | 8/1998 | Eggers |
| 5,806,517 | A | 9/1998 | Gerhardt et al. |
| 5,852,058 | A | 12/1998 | Cooke et al. |
| 5,860,938 | A | 1/1999 | Lafontaine et al. |
| 5,885,842 | A | 3/1999 | Lai |
| 5,891,057 | A * | 4/1999 | Chaisson et al. ............ 600/585 |
| 5,935,075 | A | 8/1999 | Casscells et al. |
| 5,945,452 | A | 8/1999 | Cooke et al. |
| 5,980,705 | A | 11/1999 | Allen et al. |
| 6,002,817 | A | 12/1999 | Kopelman et al. |
| 6,019,777 | A * | 2/2000 | Mackenzie ............... 604/96.01 |
| 6,100,096 | A | 8/2000 | Bollinger et al. |
| 6,112,598 | A | 9/2000 | Tenerz et al. |
| 6,165,152 | A * | 12/2000 | Becker et al. ............ 604/96.01 |
| 6,336,906 | B1 | 1/2002 | Hammarstrom et al. |
| 6,498,941 | B1 | 12/2002 | Jackson |
| 6,615,067 | B2 | 9/2003 | Hoek et al. |
| 6,652,548 | B2 * | 11/2003 | Evans et al. ................. 606/159 |
| 6,679,906 | B2 * | 1/2004 | Hammack et al. .......... 607/105 |
| 7,025,734 | B1 * | 4/2006 | Ellis et al. ................... 600/585 |
| 2002/0072680 | A1 | 6/2002 | Schock et al. |
| 2003/0013985 | A1 | 1/2003 | Saadat |
| 2003/0028128 | A1 | 2/2003 | Tenerz |

FOREIGN PATENT DOCUMENTS

| | | |
|---|---|---|
| WO | WO9402845 | 3/1994 |

OTHER PUBLICATIONS

Barker et al., *Ratiometric and Fluorescence-Lifetime-Based Biosensors Incorporating Cytochrome C' and The Detection of Extra- and Intracellular Macrophage Nitric Oxide*, Anal. Chem., May 1, 1999, 71:1767-1772.

Barker et al., *Development and Cellular Applications of Fiber Optic Nitric Oxide Sensors Based on a Gold-Adsorbed Fluorophore*, Anal. Chem., Dec. 1, 1998, 70:4902-4906.

Barker et al., *Fiber-Optic Nitric Oxide-Selective Biosensors and Nanosensors*, Anal. Chem., Mar. 1, 1998, 70:971-976.

Barker et al., *Cellular Applications of a Sensitive and Selective Fiber-Optic Nitric Oxide Biosensor Based on a Dye-Labeled Heme Domain of Soluble Guanylate Cyclase*, Anal. Chem., Jun. 1, 1999, 71:2071-2075.

Bedioui et al., *Practical Aspects and Methodological Approaches to Achieve Electrochemical Detection of Submicromolar NO In Biological Systems*, Biosens. & Bioelectron., 1998, 13:227-230.

Bedioui et al., *Elaboration and Use of Nickel Planar Macrocyclic Complex-Based Sensors for The Direct Electrochemical Measurement of Nitric Oxide in Biological Media*, Biosens. & Bioelectron., 1997, 12:205-212.

Bennett et al., *Conductive Polymeric Porphyrin Films: Application in the Electrocatalytic Oxidation of Hydrazine*, Chem. Mater. 1991, 3, pp. 490-495.

Brovkovych et al., *Direct Electrochemical Measurement of Nitric Oxide in Vascular Endothelium*, J. Pharm. Biomed. Anal., 1999, 19:135-143.

Ehrenreich-Forster et al., *Biosensor for In-Vivo Measurement of Superoxide Radicals*, Biospektrum, 1997, 4:34-37 (English Translation).

Fiaccabrino et al., *Electrochemical Characterization of Thin-Film Carbon Interdigitated Electrode Arrays*, Analytica Chimica Acta, 1996, 326:155-161.

Heikkila et al., *A Sensitive Assay for Superoxide Dismutase Based on the Autoxidation of 6-Hydroxydopamine*, Analytical Biochemistry 75, 1976, pp. 356-362.

Hishikawa et al., *Pulsatile Stretch Stimulates Superoxide Production in Human Aortic Endothelial Cells*, Circulation, 1997, 96:3610-3616.

Lisdat et al., *Superoxide Dismutase Activity Measurement Using Cytochrome c-Modified Electrode*, Apr. 1, 1999, Anal. Chem. 71:1359-1365.

van der Loo et al., *Inactivation of Nitric Oxide by Superoxide is a Mechanism Leading to Age-Related Endothelial Dysfunction*, JACC Feb. 2000, p. 277A (Abstract).

Malinski et al., *Diffusion of Nitric Oxide in the Aorta Wall Monitored in Situ by Porphyrinic Microsensors*, Biochem. Biophys. Res. Commun., Jun. 10, 1993, 193:1076-1082.

Malinski et al., *Direct Measurement of Nitric Oxide in The Cardiovascular System*, Physiol. Res., 1996, 45:279-284.

Niebauer et al., *Local L-Arginine Delivery After Balloon Angioplasty Reduces Monocyte Binding and Induces Apoptosis*, Circulation, 1999, 100:1830-1835.

Oemar et al., *Reduced Endothelial Nitric Oxide Synthase Expression and Production in Human Atherosclerosis*, Circulation, 1998, 97:2494-2498.

Pontie et al., *Improvement in the Performance of a Nickel Complex-Based Electrochemical Sensor for The Detection of Nitric Oxide in Solution*, Sensors and Actuators, 1999, B56:1-5.

Privat et al., *Direct Electrochemical Characterization of Superoxide Anion Production and Its Reactivity Toward Nitric Oxide in Solution*, Journal of Electroanalytical Chemistry, 1997, 436:261-265.

Privat et al., *Superoxide Release From Interleukin-1β-Stimulated Human Vascular Cells: in Situ Electrochemical Measurement*, Free Radic. Biol. Med., 1999, 27:554-559.

Scheller et al., *Cytochrome C Based Superoxide Sensor for in vivo Application*, Electroanalysis, 1999, 11:703-706.

Tammeveski et al., *Superoxide Electrode Based on Covalently Immobilized Cytochrome C: Modelling Studies*, Free Radic. Biol. Med., 1998, 25:973-978.

\* cited by examiner

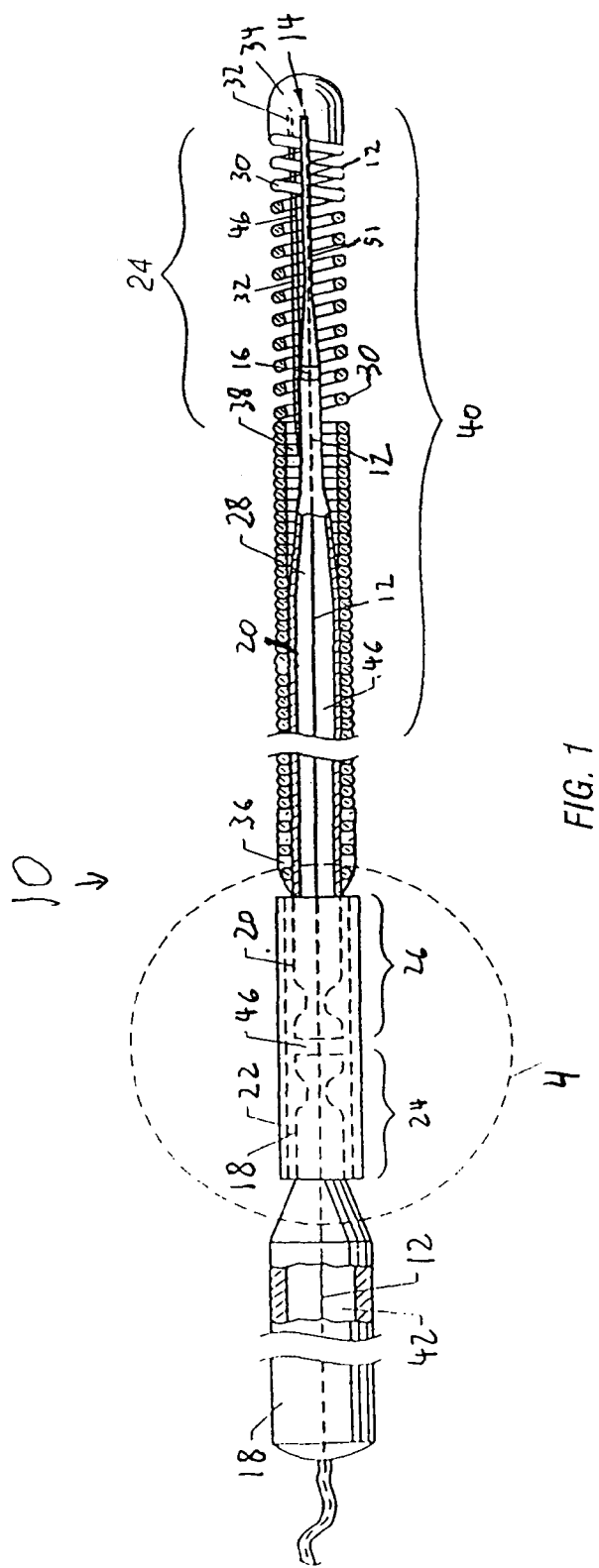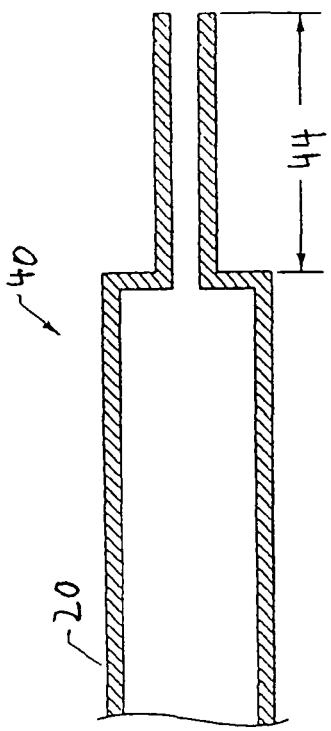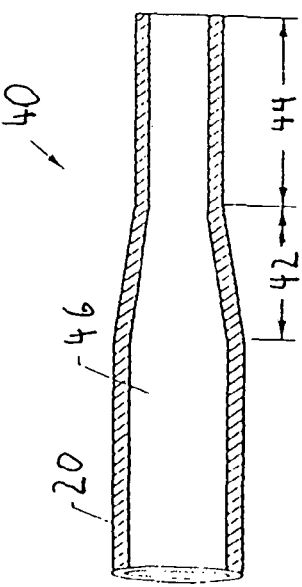
FIG. 1
FIG. 2
FIG. 3

GUIDEWIRE WITH CHEMICAL SENSING CAPABILITIES

CROSS REFERENCE

This application is a continuation of application Ser. No. 09/967,186, filed on Sep. 28, 2001, now U.S. Pat. No. 7,025,734, which is incorporated herein by reference.

BACKGROUND OF THE INVENTION

1. Field of the Invention

This invention relates to physiological sensors and methods of using the same. More particularly, this invention relates to a guidewire with a chemical sensor and a method of using the guidewire.

2. Description of the Background

Atherosclerosis refers to a thickened area in the wall of an artery which can partially or completely obstruct the vessel. Most instances of myocardial infarction, cardiac arrest, or stroke are caused by rupture, fissure, or ulceration of the atherosclerotic lesion. The rupture, fissure, or ulceration causes a large thrombus to form in the artery, which can completely occlude the flow of blood through the artery, thereby injuring the heart or brain.

Treatment modalities for atherosclerotic coronary artery disease can include percutaneous transluminal interventions (PTI) such as balloon angioplasty. PTI can relieve myocardial ischemia in patients with coronary artery disease by reducing lumen obstruction and improving coronary flow. Recurrent stenosis or restenosis, characterized by the reocclusion of the coronary artery following PTI remains a significant problem, however. Development of restenosis, typically within 6 months after the procedure, results in significant morbidity and mortality or frequently necessitates further interventions such as repeat angioplasty or coronary bypass surgery.

Reactive oxygen species in general, and the molecule nitric oxide (NO) in particular, are key entities in the processes of atherosclerosis and restenosis. In endothelial cells, NO is formed from the metabolism of L-arginine by endothelial NO synthase (Oeamar et al., "Reduced Endothelial Nitric Oxide Synthase Expression and Prosuction in Human Atherosclerosis" *Circulation* 1998, v. 97, 2494-2498). Under normal hemodynamic conditions, the production of NO inhibits such processes as monocyte adherence and chemotaxis, platelet adherence and aggregation, and vascular smooth muscle proliferation, all of which are potential causes of atherosclerosis and restenosis. In contrast, reduced NO expression has been associated with increased endothelial adhesiveness for monocytes and increased lesion formation in pathological rabbit models (Niebauer et al., "Local L-Arginine Delivery After Balloon Angioplasty Reduces Monocyte Binding and Induces Apoptosis." *Circulation* 1999, v. 100, 1830-1835). Accordingly, NO is as a key entity in the balance of metabolic and biological processes involved in atherogenesis and restenosis.

Because of the small concentrations of NO expected in vivo, a more complete understanding of sample biological environments can be obtained by making measurements of superoxide concentration in addition to or independent of NO measurements. Superoxide is a key molecular entity in determining the balance of NO released by the endothelium. Superoxide free radicals can be released by activated monocytes and can counteract NO, in effect neutralizing the beneficial properties of NO (Hishikawa and Luscher, "Pulsatile Stretch Simulates Superoxide Production in Human Aortic Endothelial Cells" *Circulation* 1997, v. 96, 3610-3616). The ratio of NO concentration to superoxide concentration can therefore be a more useful measure than either concentration alone.

Percutaneous treatment strategies for conditions such as atherosclerosis and restenosis are almost always performed without the benefit of specific knowledge of the biological environment of the lesion. While the procedures are usually initially successful, six month restenosis rates of 30% or higher are not uncommon post-procedure outcomes. Therefore, the ability to monitor the level of NO and/or superoxide present in the immediate vicinity of a lesion could provide important information necessary for a physician to obtain a clearer understanding of the relative condition of the lesion. For example, low NO and high superoxide concentrations could indicate impaired endothelium. As a result, procedures could be optimized based on individual lesion status.

Detection methods for both NO and superoxide in biological vessels and tissue are presently available. Chemoluminescent NO sensors can employ a NO sensing compound, typically containing iron, manganese, cobalt, platinum, osmium, and/or ruthenium, imbedded in a film or plug which is incorporated into the end of a fiber optic sensor. The optical characteristics of the NO sensing compound when exposed to the vessel or tissue is determinative of the NO concentration.

Other NO sensors employ methods including mass spectrometry, use of high-pressure cadmium columns (by measuring NO by-products), dithionite and hemoglobin treatment, solution methods, and electrical resistance across an electrode having a catalytic material capable of catalyzing oxidation of NO coated with a cationic exchanger. Superoxide detection methods are similar.

Accordingly, it would benefit medical professionals to be able to analyze NO and superoxide levels in vivo, and, if treatment is decided upon at the time of analysis, also begin entry of a treatment catheter with minimal additional time, energy, and medical devices.

SUMMARY OF THE INVENTION

In accordance with one aspect of the embodiments of the invention, a guidewire for biological luminal placement is provided. The guidewire includes an elongated wire assembly and a sensor for measuring the level of nitric oxide or superoxide molecules in a particular area of the patient's body. The elongated wire assembly can be configured to allow a catheter assembly to be slidably disposed over at least a portion thereof.

In one embodiment, the sensor comprises a compound that can react with nitric oxide or superoxide such that subsequent to the reaction of the compound with nitric oxide or superoxide, the optical properties of the compound change. An optical system can be provided for measuring the optical properties of the compound. The optical system can include a first fiber optic line for illuminating a light on the compound and a second fiber optic line to receive the light from the compound and to relay the received light to a detector.

In accordance with another embodiment, the sensor comprises an electrically conductive substrate having an amperometric response that is substantially unaffected by the presence of nitric oxide or superoxide and a coating for reacting with nitric oxide or superoxide so as to cause a change in the electrochemical potential of the nitric oxide or superoxide.

In one embodiment, the sensor can comprise a catalytic material capable of oxidizing nitric oxide or superoxide.

In accordance with another aspect of the embodiments of the invention, a diagnostic method is provided comprising positioning an elongated wire assembly into a vessel, the wire assembly including a sensor for measuring the level of nitric oxide or superoxide; guiding the wire assembly to a designated region within the vessel; and measuring the level of nitric oxide or superoxide in the region of the vessel. The method can further comprise inserting a catheter over the wire assembly to treat the region of the vessel. In one embodiment, a stimulant can be delivered to increase the production of nitric oxide or superoxide. The elongated wire can be used for the treatment of thrombosis or restenosis.

BRIEF DESCRIPTION OF THE DRAWINGS

FIG. 1 is a side view showing a partial cross section of an embodiment of the inventive guidewire with a chemical sensor.

FIGS. 2-3 are side views of various embodiments of the most distal part of the core section of the guidewire.

DETAILED DESCRIPTION

Figure 4:
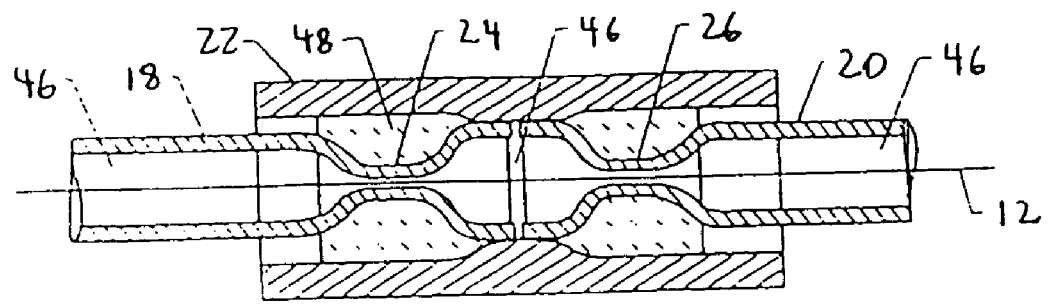
FIG. 4 is a close-up of section 4 of FIG. 1 showing the connecting element of an embodiment of the guidewire in FIG. 1.

An apparatus and method to perform therapeutic treatment and diagnosis of a patient's vasculature through the use of a guidewire having at least one chemical sensor incorporated therein are described. The inventive apparatus and method is particularly described with regard to NO and superoxide sensors used with a guidewire. The present invention is designed with the intent of use in vivo. Although the guidewire of the present invention can aid in loading a catheter for balloon angioplasty, drug delivery, or any other suitable treatment purposes, the guidewire can also act as a standalone diagnostic or treatment device.

Guidewire

FIG. 1 shows one embodiment of a guidewire 10 adapted to perform a therapeutic or diagnostic treatment. The use of the guidewire 10 is not limited to the treatment and diagnosis of a patient's vascular system, but can also include use with the esophagus, stomach, colon, uterus, joints, brain, liver, kidneys, ureter, urethra, bladder, mouth, nostrils, lungs, muscles, saphenous vein grafts or internal mammary artery grafts (and other arterial grafts such as radial grafts), and any other bodily organ capable of receiving a guidewire. Depending on the type of application in which it is to be used, the guidewire 10 can be used in conjunction with a variety of intravascular or intraluminal diagnostic or treatment devices, including balloon dilatation catheters (e.g., for percutaneous transluminal coronary angioplasty (PTCA) procedures), intravascular or intraluminal stents, directional atherectomy devices, drug delivery devices, radiation treatment devices, and devices for placing or retrieving vaso-occlusive coils.

During use of the particular embodiment in FIG. 1, a chemical sensor 12 attached to the guidewire 10 can be exposed, at the distal tip 14, to the fluid (e.g., blood) of the patient. This exposure can occur through an opening 16 of the guidewire 10. The guidewire 10 can also be operatively coupled to a variety of other diagnostic or treatment devices for organs or tissues, including intramuscular electrode devices, cerebral/cranial electro-stimulation devices, biopsy devices, drug delivery devices, radiation treatment devices, fluid drainage devices, organ implant devices, or any other diagnostic or treatment device for organs or tissues.

The guidewire 10 includes an elongated core member that includes a relatively high strength, hypotube-shaped proximal core section 18 and a relatively flexible distal core section 20. Depending on manufacturing preferences, the guidewire 10 can include a connecting element 22 that joins a distal end 24 of the proximal core section 18 and a proximal end 26 of the distal core section 20 of the guidewire 10.

The proximal core section 18 of the guidewire 10 can be generally about 130 cm (51 in.) to about 270 cm (106 in.) in length with an outer diameter of about 0.15 mm (0.006 in.) to about 0.45 mm (0.018 in.) for coronary use. Larger diameter guidewires (e.g., up to 0.89 mm (0.035 in.) or more) can be employed in peripheral arteries and other body lumens.

In the embodiment shown in FIG. 1, the distal core section 20 has at least one tapered section 28 that becomes smaller in radius with respect to the distal direction. The tapered shape of the distal core section 20 enhances the mechanical performance of the guidewire 10 by providing a stiffness gradient over the length of the distal core section 20. Alternatively, the distal core section 20 can have a non-tapered shape, which generally simplifies the manufacturing process.

In one embodiment, the proximal core section 18 and the distal core section 20 are each formed from a hypotube made of stainless steel or of a pseudoelastic alloy material, such as a nickel-titanium (NiTi) alloy (e.g., nitinol). The NiTi alloy material can include about 30% to about 52% titanium and the balance nickel and up to about 10% of one or more other alloying elements. The other alloying elements can include iron, cobalt, vanadium, platinum, palladium and copper. The alloy can, for example, contain up to about 10% copper and vanadium and up to about 3% of the other alloying elements. The proximal core section 18 can be significantly stronger than the distal core section 20. Suitable high strength materials include 304-stainless steel, which is a conventional material in guidewire construction. Other high strength materials include nickel-cobalt-molybdenumchromium alloys such as commercially available MP35N alloy.

The connecting element 22 can be configured as a sleeve or hollow member that slightly overlaps the distal end 24 of the proximal core section 18 and the proximal end 26 of the distal core section 20. Various shapes and configurations of the distal core section 20 can be practiced within the scope of this invention.

A flexible coil 30, generally having a helical configuration, can be displaced around the distal core section 20. The flexible coil 30 can be secured at its distal end to the distal end of a shaping ribbon 32 by a mass of bonding material, such as solder, which forms a rounded tip 34 when it solidifies. The proximal end of the flexible coil 30 can be secured to the distal core section 20 at a proximal location 36 and at an intermediate location 38 by a suitable bonding material. The proximal end of the shaping ribbon 32 can be secured to the distal core section 20 at the same intermediate location 38 by bonding material. The most distal section of the flexible coil 30 can be made of radiopaque metal, such as platinum or platinum-nickel alloys, to facilitate the fluoroscopic observation of the guidewire 10.

The flexible coil 30 can be about 3.0 cm (1.2 in.) to about 45 cm (18 in.) in length, more narrowly about 5.0 cm (2.0 in.) to about 20 cm (7.9 in.), can have an outer diameter about the same size as the outer diameter of the elongated proximal core section 18, and can be made from a wire of about 0.025 mm (0.001 in.) to about 0.08 mm (0.003 in.) in diameter, for example about 0.05 mm (0.002 in.) in diameter. The shaping ribbon 32 can have a generally rectangular-shaped transverse cross-section, with a width, for example, of about 0.025 mm (0.001 in.), and a height, for example, of about 0.076 mm (0.003 in.).

As shown in FIGS. 2 and 3, a distal end 40 of the distal core section 20 can be tapered and plunge-grounded to a specific length, or flattened into a rectangular cross-section (not shown). Plunge-grinding, as known by one having ordinary skill in the art, is a centered form of grinding in which the grinding tool's wheel "plunges" radially into the part. In the embodiment shown in FIG. 2, the most distal end 40 of the distal core section 20 can have a taper length 42 and a distal plunge-ground length 44. The taper length 42 can be in the range of about 4.0 cm (1.6 in.) to about 7.0 cm (2.8 in.), for example about 5.0 cm (2.0 in.). The distal plunge-ground length 44 can be typically in the range of about 6.0 cm (2.4 in.) to 10.0 cm (3.9 in.), for example about 5.0 cm (2.0 in.). The lengths 42 and 44 depend in part upon the stiffness or flexibility desired in the final product.

The outer diameter of the plunge-ground portion of the most distal end 40 can be in the range of about 0.015 cm (0.006 in.) to about 0.046 cm (0.018 in.), with one embodiment having an outer diameter of about 0.0267 cm (0.0105 in.). For the alternative embodiment having the most distal end 40 of the distal core section 20 just plunge-ground to a specific length (as shown in FIG. 3), distal plunge-ground length 44 can be the range of about 1.7 cm (0.67 in.) to about 2.2 cm (0.87 in.), for example about 2.0 cm (0.79 in.). If desired, the most distal end 40 can also be provided with a rounded tip made out of solder or other suitable material to prevent its passage through the spacing between the stretched distal section of the flexible coil 30 (shown in FIG. 1).

FIG. 4 shows a cross-sectional side view of the connecting element 22 of the guidewire 10. The connecting element 22 can be a hollow elongated element that receives the proximal end 26 of the distal core section 20 and the distal end 24 of the proximal core section 18. By facilitating the connecting element 22, the proximal core section 18 of the guidewire 10 can be in a torque transmitting relationship with the distal core section 20 of the guidewire 10. The sensor 12 can be positioned extended within a lumen 46 and disposed through the proximal core section 18, the connecting element 22, and the distal core section 20.

The connecting element 22 joining the proximal core section 18 with the distal core section 20 can be a NiTi or stainless steel sleeve. The connecting element 22 can be bonded to the distal end 24 of the proximal core section 18 and the proximal end 26 of the distal core section 20. Bonding of the connecting element 22 can be done using any method known to those having ordinary skill in the art, including laser bonding, thermal bonding, or with an adhesive 48, including adhesives cured with ultraviolet (UV) light, such as Loctite.

Figure 5:
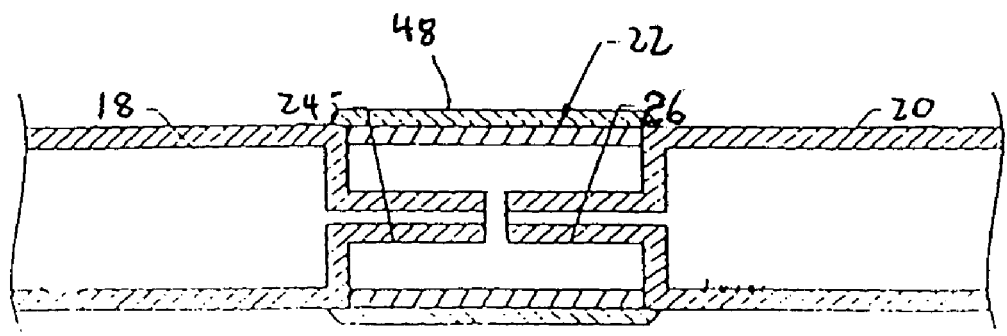
FIG. 5 illustrates another embodiment of the connecting element of the guidewire.

In the embodiment shown in FIG. 5, the connecting element 22 joining the proximal core section 18 with the distal core section 20 is a polyimide jacket (or tubing). The jacket can be bonded to the distal end 24 of the proximal core section 18 and the proximal end 26 of the distal core section 20 with the adhesive 48.

The connecting element 22 generally has an outer diameter in the range of about 0.025 cm (0.010 in.) to about 0.089 cm (0.035 in.), with an inner diameter in the range of about 0.020 cm (0.008 in.) to about 0.084 cm (0.033 in.). The overall length of the connecting element 22 can be in the range of about 0.25 cm (0.098 in.) to about 3.0 cm (1.2 in.), more narrowly in the range of about 0.75 cm (0.30 in.) to about 1.5 cm (0.59 in.).

Figure 6:
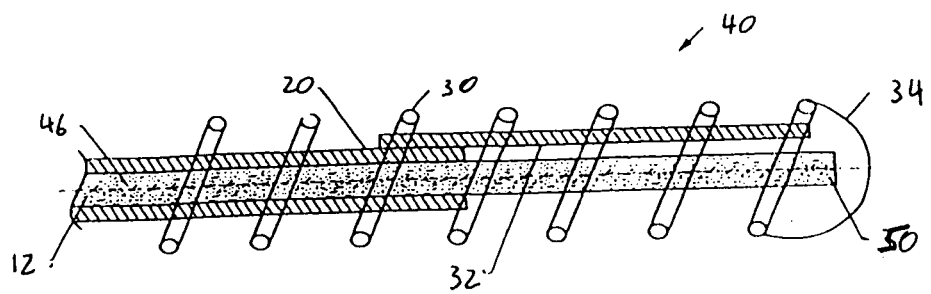
FIGS. 6-9 illustrate various embodiments of the distal end section of the distal core.
Figure 7:
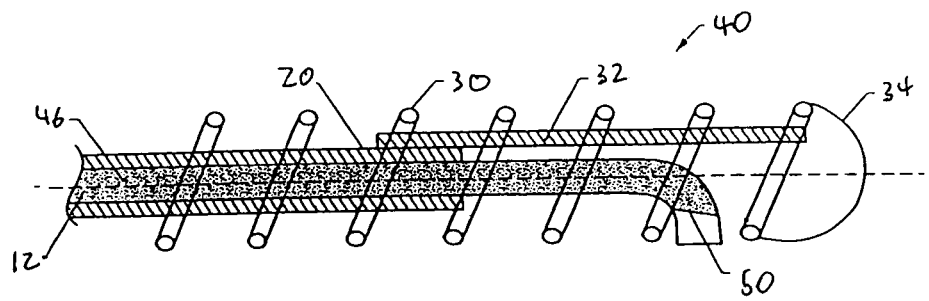

In FIGS. 6-9, various alternate embodiments of the distal end 40 of the guidewire 10 are illustrated. FIG. 6 illustrates an embodiment with the shaping ribbon 32 inserted under the flexible coil 30, overlapping the distal end 40 of the distal core section 20. The shaping ribbon 32 can then be soldered in place. Further, a chemical sensor tip 50 can be disposed within the lumen 46 and distally ends in the rounded tip 34.

The rounded tip 34 of the guidewire 10 can be a clear polymeric atraumatic tip formed by coupling a clear polymeric material sheath or tube to the flexible coil 30. Alternatively, the rounded tip 34 can also be a metal atraumatic tip. The metal tip can be formed by the soldering material used to couple the distal end of the flexible coil 30 to the shaping ribbon 32. With either the metal or polymeric tip configuration, the chemical sensor tip 50 disposed within the lumen 46 can be bent away from the centerline of the distal end 40 to potentially improve chemical reception (illustrated in FIG. 7).

Figure 8:
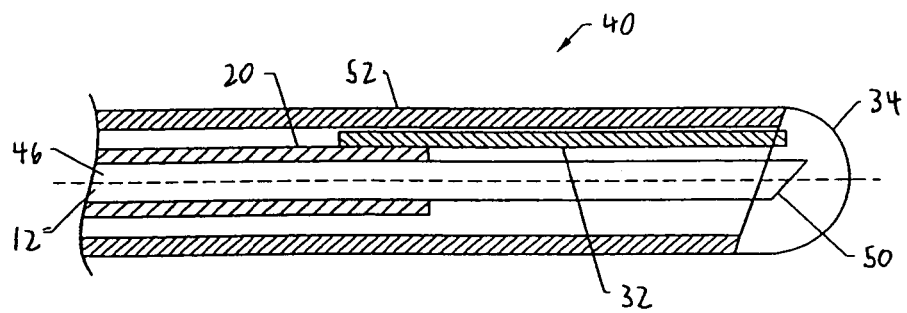
Figure 9:
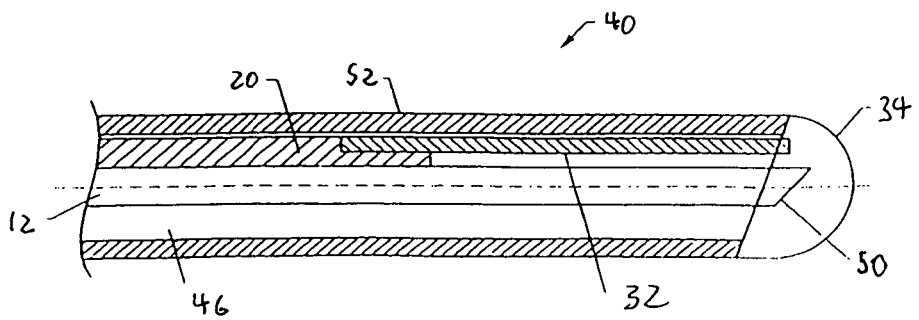

In FIGS. 8 and 9, the sensor 12 extends longitudinally through the lumen 46 of a polymeric jacket 52. In FIG. 9, the distal core section 20 can be in the form of a reinforcing mandrel.

Catheter

In the embodiments shown herein, the guidewire 10 can be constructed to be able to receive a catheter. The catheter typically slides longitudinally along and over the guidewire 10. The inside diameter of the catheter can be larger than the outside diameter of the guidewire 10 to provide for sliding.

Any treatment or diagnosis catheter or device with an appropriately sized and shaped lumen can be used with the guidewire including drug delivery catheters, scopes (endoscopes, arthroscopes, laproscopes, cardioscopes, etc.), dilatation catheters (e.g. balloon catheters), vaso-occlusive coil delivery and/or retrieval devices, stent delivery devices (including balloon dilatation catheters), implant delivery and/or retrieval devices, etc.

Drug delivery catheters or stents can be used to administer any number of active agents. The active agent can be for inhibiting the activity of vascular smooth muscle cells. More specifically, the active agent can be aimed at inhibiting abnormal or inappropriate migration and/or proliferation of smooth muscle cells for the inhibition of restenosis. The active agent can also include any substance capable of exerting a therapeutic or prophylactic effect in the practice of the present invention. For example, the agent can be for enhancing wound healing in a vascular site or improving the structural and elastic properties of the vascular site. Examples of agents include antiproliferative substances such as actinomycin D, or derivatives and analogs thereof (manufactured by Sigma-Aldrich 1001 West Saint Paul Avenue, Milwaukee, Wis. 53233; or COSMEGEN available from Merck). Synonyms of actinomycin D include dactinomycin, actinomycin IV, actinomycin $I_1$, actihomycin $X_1$, and actinomycin $C_1$. The active agent can also fall under the genus of antineoplastic, anti-inflammatory, antiplatelet, anticoagulant, antifibrin, antithrombin, antimitotic, antibiotic, antiallergic and antioxidant substances. Examples of such antineoplastics and/or antimitotics include paclitaxel (e.g. TAXOL® by Bristol-Myers Squibb Co., Stamford, Conn.), docetaxel (e.g., Taxotere®, from Aventis S. A., Frankfurt, Germany) methotrexate, azathioprine, vincristine, vinblastine, fluorouracil, doxorubicin hydrochloride (e.g., Adriamycin® from Pharmacia & Upjohn, Peapack N.J.), and mitomycin (e.g., Mutamycin® from Bristol-Myers Squibb Co., Stamford, Conn.). Examples of such antiplatelets, anticoagulants, antifibrins, and antithrombins include sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, and thrombin inhibitors such as Angiomax a (Biogen, Inc., Cambridge, Mass.). Examples of such cytostatic or antiproliferative agents include angiopeptin, angiotensin converting enzyme inhibitors such as captopril (e.g., Capoten® and Capozide® from Bristol-Myers Squibb Co., Stamford, Conn.), cilazapril or lisinopril (e.g., Prinivil® and Prinzide® from Merck & Co., Inc., Whitehouse Station, N.J.), calcium channel blockers (such as nifedipine), colchicine, fibroblast growth factor (FGF) antagonists, fish oil (omega 3-fatty acid), histamine antagonists, lovastatin (an inhibitor of HMG-CoA reductase, a cholesterol lowering drug, brand name Mevacor® from Merck & Co., Inc., Whitehouse Station, N.J.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), and nitric oxide. An example of an antiallergic agent is permirolast potassium. Other therapeutic substances or agents which can be appropriate include alpha-interferon, genetically engineered epithelial cells, rapamycin and dexamethasone.

Chemical Sensors

Referring again to the embodiment in FIG. 1, the sensor 12 can be fixedly coupled to the guidewire 10 at least at one coupling location 51. Alternatively, the sensor 12 can be operatively coupled to the guidewire 10. In this configuration, the sensor 12 can be longitudinally slideable, transversely shiftable, and rotationally movable within the guidewire 10.

In one embodiment, the sensor 12 can have an outer diameter in the range of about 10 µm to about 1000 µm. Other sensor diameters are also within the scope of this invention, including those of approximate outer diameters of 30 µm, 200 µm and 250 µm. Regardless of diameter, sensors can provide the guidewire 10 with the ability to sense vessel and blood characteristics, including but not limited to concentration, density, gross volume, mass, molarity, and/or particle count of NO and/or superoxide and other oxygen containing molecules.

The sensor 12 can extend longitudinally through the lumen 46 of the distal core section 20 of the guidewire 10 as well as through the connecting element 22 and the proximal core section 18. For the embodiment shown in FIGS. 8 and 9, the sensor 12 extends longitudinally through the polymeric jacket 52, immediately below the distal core section 20, as well as through the connecting element 22 and the proximal core section 18. In the embodiment shown in FIG. 9, the distal core section 20 can be in the form of a reinforcing mandrel.

As stated above, in one embodiment, the sensor 12 can be exposed to a blood vessel of a patient at the distal tip 14 of the guidewire 10 or through the opening 16. The opening 16, such as a window or a cutaway, allows the sensor 12 to be exposed to a patient's vasculature and perform its intended sensing function. The opening 16 can have any size and/or shape that is advantageous to sensor 12 and/or the guidewire manufacturing preferences.

It is understood, however, that the sensor 12 can extend longitudinally along either the inside or outside of the proximal core section 18, the connecting element 22 and the distal core section 20. The sensor 12 can extend beyond both ends of the guidewire 10. The sensor 12 can be in communication with a data processing system through a mechanical coupler. The distal extension of the sensor 12 allows the sensor tip 50 to be flush with, or extend slightly out of the distal end 40 of the guidewire 10.

NO Optical Sensors

Figure 10:
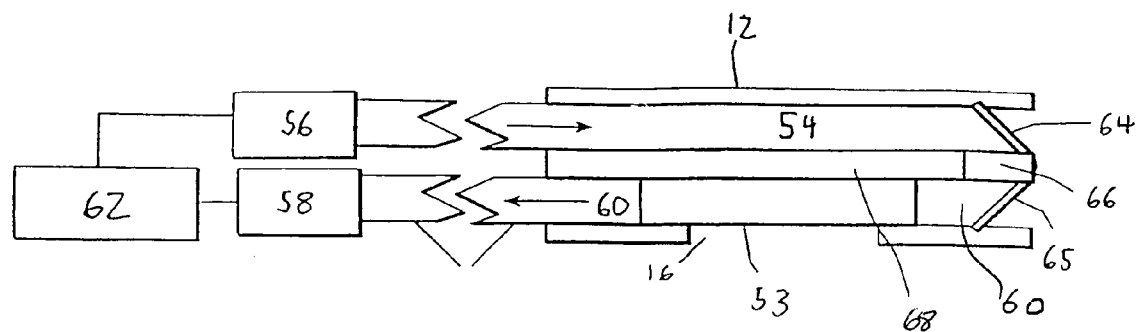
FIGS. 10-11 illustrate various fiber optic embodiments of the chemical sensor.
Figure 11:
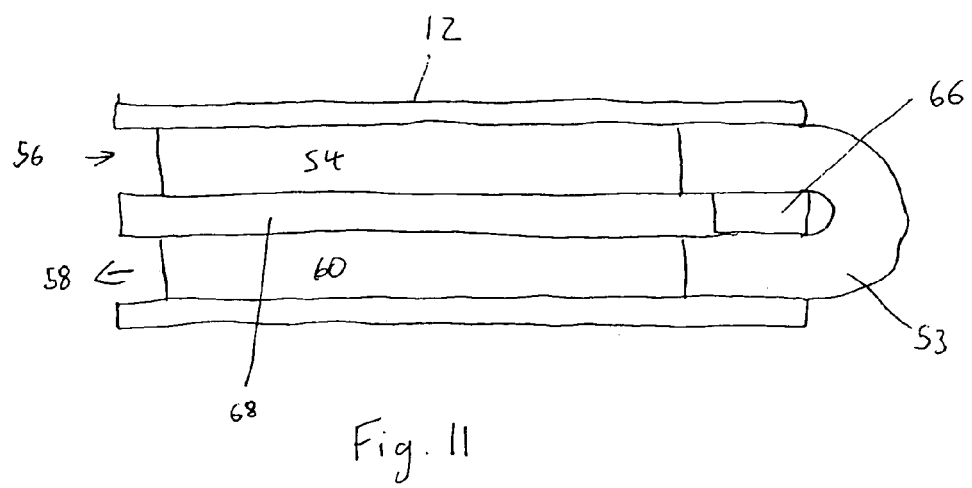

As shown in FIGS. 10 and 11, the sensor 12 can be an optical NO sensor. The optical NO sensor can have a polymer matrix film or plug 53 incorporated into an optical fiber sensor system. NO-sensing compounds exhibiting sensitivity and selectivity to NO are imbedded in the polymer matrix film or plug 53. The optical properties of the NO-sensing compounds change upon reaction with NO. NO-sensing compounds that act reversibly or irreversibly with NO can be selected for use in the sensor 12.

The NO-sensing compound can be selected from an appropriate porphyrin compound or metal-containing compound such as metalloporphyrins. Possible metals include iron, manganese, cobalt, platinum, osmium, and ruthenium. For example, iron-containing compounds suitable for use include hemes, of which the compound can include oxyhemoglobin, cytochrome c, hemin, and myoglobin.

A flexible and modular optical system can be required for development of the sensor 12. Such an absorption-based system can deliver light into an optical fiber 54, usually made of silica (glass) or plastic, to excite the sensor 12, efficiently collect the returned light, and convert it to NO concentration. As needed, signal processing can be incorporated into the system to eliminate system noise or background. The optical system can also be used with fluorescent or phosphorescent sensors under conditions in which luminescent sensors are to be used.

In specific applications, the optical system would include diodes at specific wavelengths and no grating. In a general description of one system, the components of the optical system are optimized for fiber optic output from a light source 56 and fiber optic input to a detector 58. These components, connected by SMA connectors, include:

(1) Fibers 54 and 60. 100 µm silica core, silica clad fibers can be used in the optical system. Other sizes can also be used including fibers as small as about 100 nm to about 1000 nm and fibers in the range of about 1 µm to about 100 µm.

(2) Light source 56. The sensor design utilizes a continuous tungsten halogen lamp. This lamp can be replaced with a pulsed source or a chopper can be placed in front of the lamp under conditions where photodegradation of sensor compounds is determined to occur, or under conditions where synchronization of the source 56 and a detector 58 is desirable to filter out background noise.

(3) Detector 58. A 1200 lines/mm grating over the range of 400-650 nm disperses light onto a 1024 element CCD detector with a resolution of about 1 nm to about 2 nm. This level of resolution can be adequate for most expected uses of the NO sensor. If improved resolution is required, the grating can be changed, or the diameter of the fiber which goes to the detector and acts as the entrance slit of the spectrometer can be reduced.

(4) A data system 62. The detector 58 can be connected to a PC through a National Instruments A/D board. The spectrometer and acquired data can be driven by Spectrasoft software (World Precision Instruments). This software, based on LabView software, which is known to those having ordinary skill in the art, can be used to determine the best method of reading data from the CCD to achieve the desired sensitivity. For example, the signal to noise ratio can be altered by use of LabView software signal processing algorithms if necessary. LabView software can also be used to perform sensor calibration and display real-time values of NO concentrations. Proper sensor design and signal processing in the above described optical system allows sensitivity of a 0.0001 absorbance unit change in absorbance equivalent to be achieved.

FIG. 10 shows one embodiment of the sensor 12 design. This dual lumen sensor includes the optic fibers 54 and 60. The sensor 12 has an outer diameter less than 1.0 mm (0.039 in.) as a housing for the two fibers 54 and 60. The distal ends of the fibers 54 and 60 can be cut and polished at about a 45 degree angle, and aluminum or gold evaporated onto the polished surface to form two mirrors 64 and 65. The fiber 54 transmits light from the light source 56 to the mirrors 64 and 65. Light travels from the source 56 through fiber 54, is reflected by the mirror 64, travels through the transparent plug 66, then reflects off the mirror 65, through the fiber 60, through the plug 53 (which is inserted between two sections of fiber 60), and back through fiber 60 to the detector 58. Light output and input can then be processed by the data system 62.

The length of the section removed from the fiber 60 is a control for the path length of the absorbing compound, and can be varied as needed to optimize sensor performance. The NO-sensing compound can be injected into a mold containing the sensor 12 and allowed to cure, forming a semi-rigid NO-permeable plug. The fiber with the second mirror (fiber 60 in the embodiments shown in the figures) can be aligned before the gel is cured and fixed in place. Prior to assembly, a portion of the sidewall of the sensor 12 can be removed forming the opening 16 that allows NO gas to permeate to the sensing compound. A notch can be removed from the center of the sensor forming a gap 68 for light to be reflected between the two fibers. The gap 68 can be filled with the transparent plug 66.

FIG. 11 shows another variation of this embodiment placing the plug 53 at the distal tip of the sensor 12. This removes the need for mirrors 64 (shown in FIG. 10). Placing the plug 53 at the distal tip of the sensor 12 also provides chemical sensitivity at the most distal point of the sensor 12.

Variations of this embodiment exist. For example, the exposed portion of the plug 53 can have a coating imbedded with NO-sensing protein. The coating can be relatively inert to NO, such as a particular metal or metal colloid including gold, silver, tungsten, thoriasol, antimony pentoxide, carbon, red iron oxide, titanium dioxide and platinum. Colloid sizes from 2 nm to 250 nm, and more narrowly of the range from 5 nm to 100 nm, provide a foundation for protein attachment. Protein(s) and/or peptide(s) that are dye labeled are then attached to the metal foundation. The dyes, such as Orange Green fluorophore dyes, can be used for protein and/or peptide labeling but should not react to NO.

The protein and/or peptide bind NO. They can also bind NO specifically. Binding specifically is the act of binding with NO, but not binding with interfering substances. One useful heme-group-containing protein is cytochrome c'. Some sources of cytochrome c' include, but are not limited to, microorganisms, more preferably bacterial sources, and more particularly, purple phototropic bacteria, aerobic nitrogen-fixing bacteria, and facultatively denitrifying bacteria, and still more particularly sources such as *C. vinosum, R. purpureus*, and *R. gelatinosa*. The NO-binding compound can also be entrapped in a matrix, such as a silica sol. Furthermore, stabilizers can be used in the compound.

NO Electrode Sensors

One embodiment of the sensor 12 can be an electrode or multiple electrodes having a catalytic material capable of catalyzing oxidation of NO coated with a cationic exchanger. These electrodes can be wires acting as the whole length of the sensor and/or electrodes mounted at the end of the sensor 12. The sensor 12 provides a direct measurement of NO through the redox reaction of $NO \rightarrow NO^+ + e^-$ and is selective for NO through the discrimination of the cationic exchanger against nitrite ($NO_2^-$).

Specifically, the NO-specific electrode sensor comprises an electrically conductive substrate whose amperometric response is substantially unaffected by the presence of NO. The electrode also comprises an adherent and substantially uniform electrochemically active polymeric coating which interacts with NO in such a manner so as to cause a change in the redox potential of NO and the electrode sensor.

The electrically conductive substrate can be electrically conductive carbon (e.g., basal plane carbon, pyrolytic graphite (BPG), or glassy carbon), indium tin oxide, iridium oxide, nickel, platinum, silver, or gold. The preferred electrically conductive substrate will depend in part on whether oxidation or reduction at the electrode sensor will be taking place during use. For example, a noble metal such as platinum or gold could evolve hydrogen from water reduction which could adversely affect the polymer film(s) on the substrate.

This oxidation potential for NO on a standard electrode can be lowered by contact with various materials capable of catalytically oxidizing NO. The current or charge generated by this embodiment can be high enough to be used as an analytical signal in a microsystem. A working electrode of this embodiment can have a conductive solid support with a catalytic surface for NO oxidation. A catalytic surface on a conductive support can be provided using several approaches.

For example, a conductive catalytic material capable of catalyzing NO oxidation can be layered on a conductive solid support. The conductive catalytic material can be layered on any number of conductive materials coated on a conductive or nonconductive base material; the conductive catalytic material can be layered directly on a conductive base material; or the conductive catalytic material can itself comprise the conductive support. The electrode can also be fashioned directly from the conductive catalytic material or by incorporating or doping a catalyst into the support material. A working electrode of a sensor of the described embodiment of this invention preferably can have a solid conductive support coated with one or more layers of a conductive material capable of catalyzing oxidation of NO, hereinafter referred to as catalytic material.

Several types of catalytic materials can be used in the sensor, as long as the catalytic material exhibits electronic, ionic or redox conductivity or semiconductivity, collectively referred to herein as conductivity. The change in the observed current drawn through the electrode sensor at a particular potential can be correlated to the concentration of NO in the sample being evaluated. Such materials include, but are not limited to, polymeric porphyrins and polypthalocyanines. The above-mentioned materials can contain central metals, including transition or amphoteric metals. The metallized or doped polymer can contain any suitable metal which will interact with NO, such as the transition or amphoteric metals and preferably nickel, cobalt, or iron. Polymers which can also be used but require doping include polyvinylmetallocenes (e.g. ferrocene), polyacetylene doped with different metal redox centers and polypyrraline doped with different redox centers such as, e.g. methyl viologen. Polymeric substituted glyoximes can also be employed.

Figure 12:
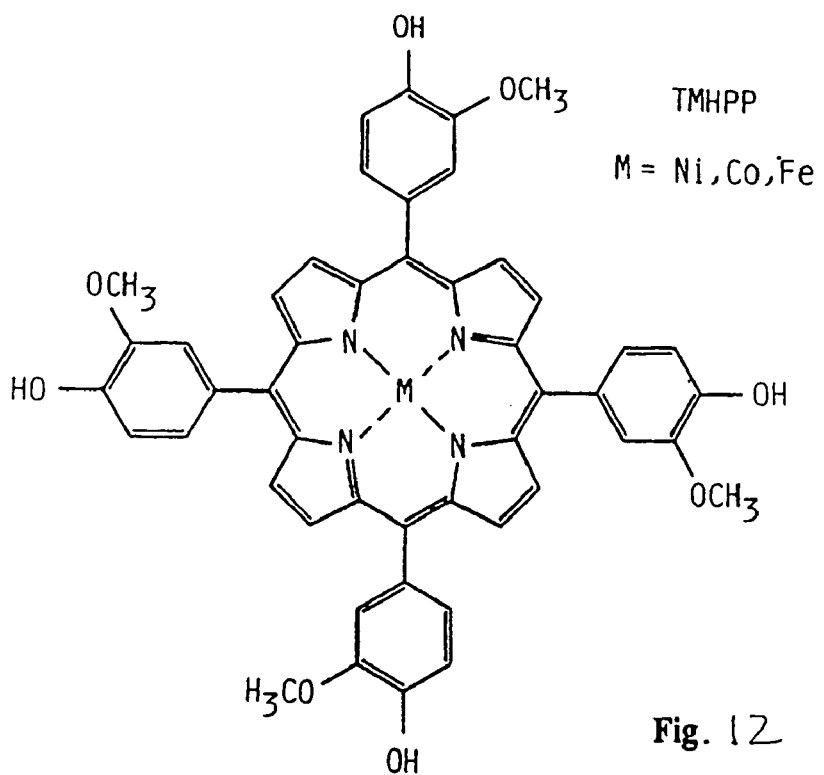
FIG. 12 shows a monomeric porphyrin structure that can be used in an embodiment of the chemical sensor.
Figure 13:
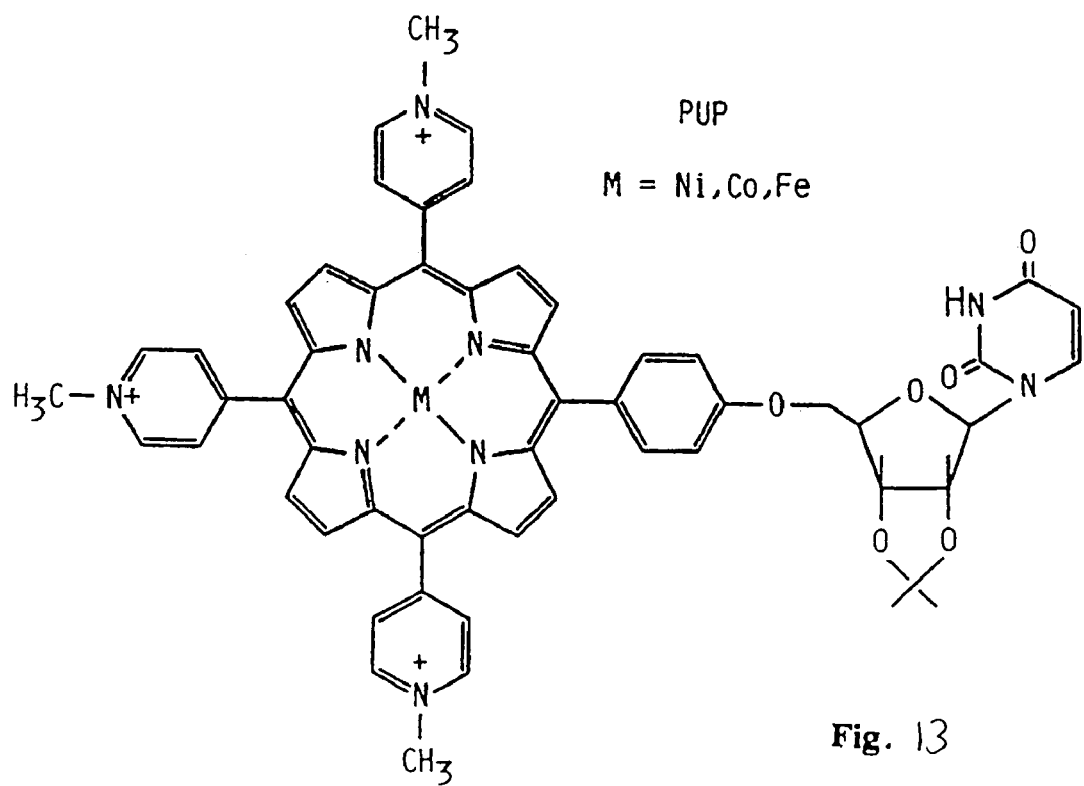
FIG. 13 shows another monomeric porphyrin structure that can be used in an embodiment of the chemical sensor.

Catalytic conductive materials that can be used for a sensor of the present invention are metallized polyphthalocyanine or polymeric metalloporphyrins, which are organic p-type semiconductors with relatively high conductivity and which can be successfully deposited on a supporting conductive material. The metallized polymeric porphyrin compounds should not form metal-oxo bridges (M-O-M) with the substrate. Polymeric metalloporphyins have been shown to have high catalytic effect for the electrochemical oxidation of several small organic and inorganic molecules. Bennett, J. E. et al., Chem. Materials 3:490-495 (1991). Polymeric porphyrins polymerized and copolymerized from monomeric porphyrins N,N'-di(5-p-phenylene-10,15,20-tri(3-methoxy-4-hydroxyphenyl)porphyrin, 1,10,-phenantroline-4,7-diamine, and 5-p-(pyrole-1-yl) phenylene-10,15,20-tri-(3-methoxy-4-hydroxyphenyl)porphyrin with Fe, Mn, Co and Ni as central metals are useful for this embodiment given their high catalytic effect for selective electrochemical oxidation of NO. Other useful compounds include tetrakis(3-methoxy-4-hydroxyphenyl) porphyrin (TMHPP) and meso-5'-0-p-phenylene-2',3'-0-isopropylidene uridine-tri(n-methyl-4-pyridinium)porphyrin (PUP), shown in FIGS. 12 and 13.

Figure 14:
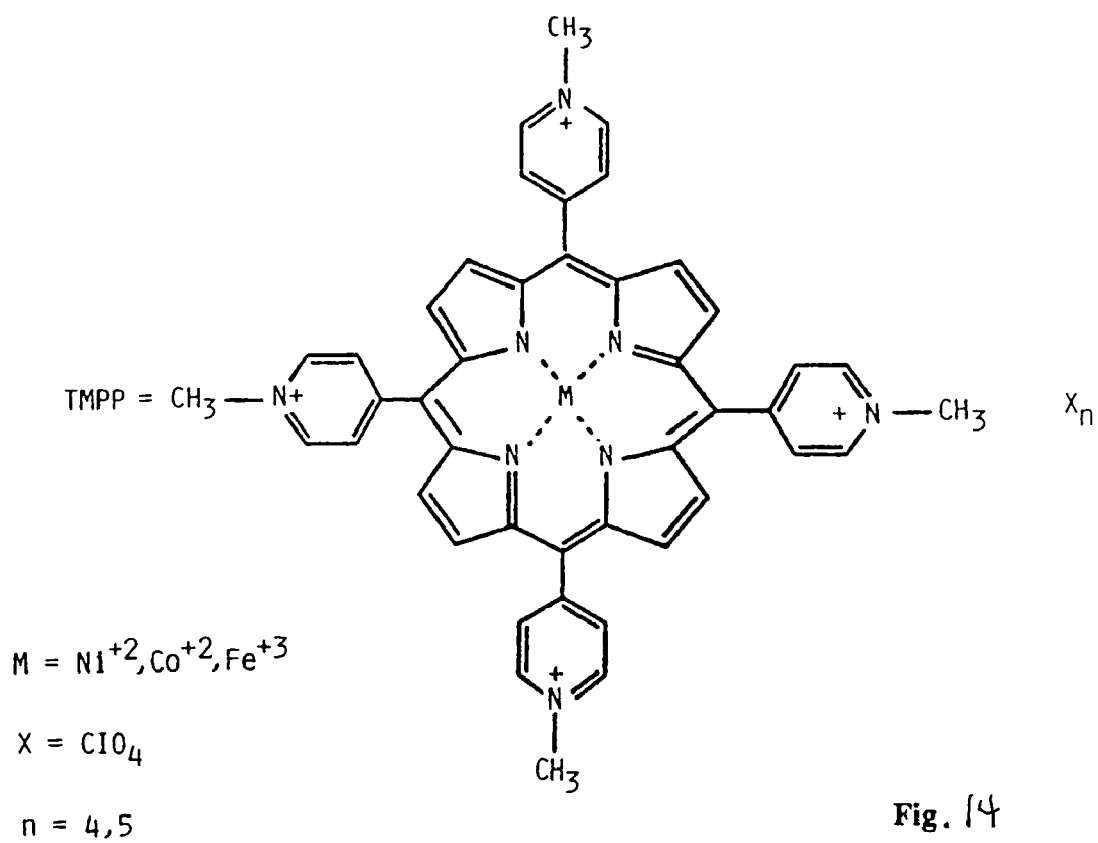
FIG. 14 shows a tetramethylpypridylporphyrin (TMPP) structure that can be used in an embodiment of the chemical sensor.
Figure 15:
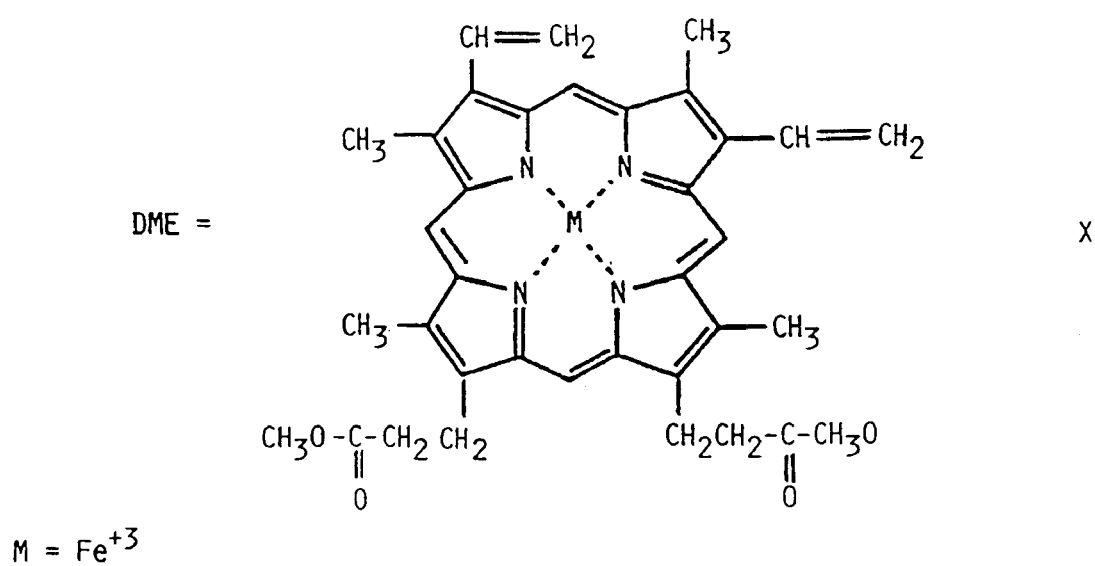
FIG. 15 shows a protoporphyrin IX dimethyl ester (DME) structure that can be used in an embodiment of the chemical sensor.

The electrochemically active polymeric coating also can be comprised of the metallized polymeric porphyrin compounds of tetramethylpyridine pyrrole and dimethyl ester porphyrin, especially tetramethylpyridine pyrrole (TMPP) and dimethyl ester porphyrin (DME) metallized with nickel, cobalt, and iron. Metallized porphyrin compounds of TMPP and DME are respectively depicted in FIGS. 14 and 15, wherein M is any suitable metal ion, such as $Ni^{2+}$, $Co^{2+}$, or $Fe^{3+}$, X is a suitable anion to render the compound neutral, such as $ClO_4^-$ in the case of TMPP and $Cl^-$ in the case of DME, and n is an integer sufficient to render the compound neutral, such as 4 in the case of $Ni^{2+}$ and $Co^{2+}$ TMPP, 5 in the case of $Fe^{3+}$ TMPP, and 1 in the case of $Fe^{3+}$ DME (not shown).

The electrochemically active polymeric coating should be adherent to and substantially uniform over the substrate. While the polymeric coating can be of any suitable thickness, a suitable example range is between about 0.01 μm and about 50 μm in thickness. Electrochemically active polymeric coatings will differ in affinity for various substrates. The electrochemically active polymeric coating as used in the present inventive electrode sensor preferably has a high affinity for the particular substrate being used.

In order to discriminate against interfering ions and compounds, particularly $NO_2^-$, the porphyrinic catalysts used in the present invention are also preferably covered with a thin layer of a cationic exchanger or gas-permeable membrane to prevent anion diffusion to the catalytic surface. The gas-permeable membrane coating can be of any suitable material, preferably a perfluorinated compound such as Nafion® (available from Aldrich Chemical Co., Milwaukee, Wis.), a fluorocarbon polymer. Suitable cationic exchangers include AQ55D available from Kodak and the stated Nafion®. Nafion® is a negatively charged cationic exchange polymer which prevents diffusion of anions like $NO_2^-$ to the electroactive surface of the polymeric porphyrin, but is highly permeable to NO. The layer of cationic exchanger or gas-permeable membrane coating deposited onto the surface of the electrode sensor can be of any suitable thickness, including from about 0.5 μm to about 50 μm. The resulting membrane-coated NO electrode sensor is more selective to NO than an uncoated electrode due to the membrane exclusion of interfering species such as nitrite.

The thin layer of polymeric porphyrin film can be electrochemically deposited on any solid conductive support, or a conductive or nonconductive base material coated with any number of conductive materials, or the conductive catalytic material can itself comprise the conductive support. Conductive support materials particularly suitable for these sensors include carbon fibers, and gold or platinum wire.

The NO-specific electrodes can be prepared in any suitable manner. An adherent and substantially uniform coating of an electrochemically active polymer, as previously described, can be formed on a surface of an electrically conductive substrate, as previously described, by any suitable means including electrolytic polymerization.

For electrolytic polymerization, the precursor (e.g., monomer, dimer, or oligomer) used to form the electrochemically active polymeric coating can be electrolytically polymerized onto a surface of the electrically conductive substrate. This electrolytic polymerization occurs by immersing the substrate in an appropriate electrolyte solution containing the precursor in combination with a supporting electrolyte. The electrolyte solution will typically additionally contain a suitable solvent. Examples of solvents that can be used in the electrolyte solution include acetonitrile, methanol, dimethyl formamide, dimethyl sulfoxide, propylene carbonate, and the like. The supporting electrolyte can be a perchlorate, sulfuric acid, phosphoric acid, boric acid, tetrafluoro-potassium phosphate, quaternary ammonium salt, or similar compound.

The coating of the gas-permeable membrane (e.g., Nafion®) can be applied onto the sensor by any suitable means. For example, a solution of the membrane material (e.g., Nafion®) can be used to coat the electrode, and the electrode then can be allowed to dry to produce a uniform film. The sensitivity of the gas-permeable membrane-coated electrode sensor can be further increased by soaking the electrode sensor in a sodium hydroxide solution for at least about 24 hours and preferably a few days.

During use, NO will directly interact with or bind the polymeric coating on the substrate, thereby changing the redox potential of NO and the electrode sensor. This interaction changes the current drawn through the electrode sensor when employed as a working electrode at a particular potential in a manner related to the concentration of NO in the sample being evaluated. For example, metalloporphyrins, which contain metals such as iron, manganese, nickel, and cobalt, are capable of binding NO and are believed to form metal nitrosyls which provide a different oxidation or reduction potential than NO or the electrode sensor alone. The NO concentration in a sample can be determined by comparing the observed current drawn through the electrode sensor as a working electrode at a fixed potential with the currents observed at the same potential using reference samples with a known NO concentration.

In measuring NO, a two or three electrode system can be employed. The working electrode, comprising the coated carbon fiber, with mesh or plate, can be connected to a conductive lead wire with conductive epoxy. The lead wire connects to the voltammetric analyzer, potentiostat or coulometric measuring instrument. The auxiliary or counterelectrode generally comprises a chemically inert conductive material such as a noble metal, carbon or tin indium oxide which can also be connected to the measuring instrument with a lead wire. In a three electrode system, a reference electrode, such as a standard calomel electrode (SCE), can also be employed and connected to the measuring instrument with a third conductive lead wire.

The method of detecting the presence or absence of NO in a sample, therefore, comprises connecting the NO-specific electrode sensor of the present invention to a potentiostat, calibrating the potentiostat and electrode sensor for a sample known to be devoid of NO, and detecting the presence or absence of NO in an unknown sample by comparing the measured current to the current for the sample known to be devoid of NO. A change in the observed current indicates the presence of NO in the unknown sample. Similarly, the method of measuring the concentration of NO in a sample comprises connecting the NO electrode sensor to a potentiostat, calibrating the potentiostat and electrode sensor for samples of known NO concentration, and measuring NO concentration in an unknown sample by comparing the measured current to the current for the samples of known NO concentration.

The potential applied to the electrode will depend upon the type of polymeric compound used to coat the substrate. The applied potential can have a greater absolute value than the peak potential of the oxidation or reduction reaction in a cyclic voltammogram (e.g., a −0.45 V applied potential for a −0.40 V peak potential, or a +0.55 V applied potential for a +0.50 V peak potential), all relative to a reference electrode potential.

The detection and/or measurement of NO in a sample can also be accomplished by contacting the electrode sensor with the sample for some determined period of time sufficient to allow interaction of NO with the electrochemically active polymeric coating. The electrode sensor can then be removed from the sample. Readings from a potentiostat previously calibrated for known concentrations of NO, and comparing the observed current with the current for the electrode sensor having been exposed to similar samples of known NO concentration for the same period of time.

In a variation of this embodiment, the electrode(s) can be prepared from ruthenium, or have a coating prepared from ruthenium on a core of supporting material. Alternatively, the ruthenium can be combined with one or more metals or non-metals as may be desired.

The body of the electrode(s) can also be wrapped with electrical shielding. The electrical shielding would not cover the portion of the electrode used to contact the sample. The electrical shielding would reduce interference. Reduction of interference can be useful on numerous occasions including using the electrode near RF medical devices, such as electrocauterization devices.

Superoxide Sensors

The above embodiments can be used for superoxide sensors with minor modifications. Superoxide sensors generally use different chemoluminescent and electrically reactive chemicals than NO sensors. Reactive chemoluminescent and electrically reactive methods for superoxide fiber optic sensors include nitro blue tetrazolium ($NO_2$-TB) method, cytochrome c method, epinephrine method, pyrogallol method and 6-hydroxydopamine method (Heikkla et al., *Anal. Biochem.* 75: 356-362, 1972), and $H_2O_2$ measurement method, all of which are commonly used in the art.

The principle of these superoxide dismutase (SOD) activity determination processes is shown, for example, by taking the case of a process using the $NO_2$-TB method in superoxide detection system. When SOD is present in the system, dismutation of superoxide is accelerated and the superoxide produced becomes $O_2$ and $H_2O_2$. This superoxide also reduces cytochrome c, $NO_2$-TB or the like to subject the same to coloration and oxidizes epinephrine, pyrogallol, 6-hydroxydopamine or the like to subject the same to coloration. Therefore, by utilizing this property, a decrease in absorbance of sample with respect to reagent blank value is measured and SOD activity value can be determined.

Measuring the $H_2O_2$ produced by the action of SOD can also be a suitable method of determining superoxide levels with the sensor 12 of the guidewire 10. As a method and a reagent for quantitating $H_2O_2$ in the SOD activity determination process of this invention, any conventional method and reagent quantitating $H_2O_2$ can be used. For example, all methods for quantitating $H_2O_2$ by combination of peroxidase and an oxidizable color reagent can be used. Such oxidizable color reagents include, for example, oxidizable color reagents consisting of a combination of 4-aminoantipyrine (4-AAP) and a phenolic compound or an N,N-disubstituted aniline series compound, combined reagents of 3-methylbenzothiazolinonehydrazone (MBTH) and an aniline series compound, 2,2'-azinobis(3-ethylbenzothiazoline-6-sulfonic acid) (ABTS), triphenylmethane series leuco coloring materials, benzidine derivatives, o-tolidine derivatives, diphenylamine derivatives, triallylimidazole derivatives, o-phenylenediamine, leucomethylene blue derivatives, etc. In addition to the methods described above, a method using a combined reagent of a tetravalent titanium compound and 2-(5-bromo-2-pyridylazo)-5-(N-propyl-N-sulfopropylamino)phenol and/or a salt thereof (which can avoid using POD) can also be used for quantitating $H_2O_2$. For further stabilizing the oxidizable color reagent and its developed color after oxidation and coloration, the presence of β-cyclodextrin and/or a derivative thereof or of γ-cyclodextrin can be sufficient.

With respect to the concentrations of these compounds, a concentration of β-cyclodextrin of 0.01 to 1.5 wt/vol %, that of γ-cyclodextrin of 0.1 to 3 wt/vol %, that of β-cyclodextrin derivative of 0.1 to 5 wt/vol % and that of γ-cyclodextrin derivative of 0.1 to 5 wt/vol % can all be used in the solution. Mixtures of two or more of these compounds in any ratio can also be used so long as the concentrations of the compounds are within the above-mentioned ranges.

The cyclodextrin derivative includes:

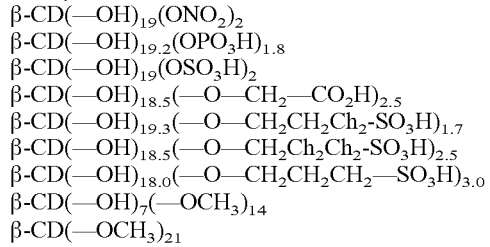

Although all of the above listed methods for measuring superoxide levels are well suited for use with a fiber optic detector, as described with respect to NO fiber optic sensors above, they can also be used as coatings on an electrode to measure electrical resistance as described above for NO electrode sensors.

Additional Sensors

Other sensors can be used in addition to NO and/or superoxide sensors, including those for sensing hemodynamic characteristics, hematological parameters related to blood and blood components, and thermal parameters of the vasculature, lesion, or body site being treated. Sensors capable of these supplemental measurements are commonly known to those having ordinary skill in the art and include fiber optic sensors.

Possible target hemodynamic characteristics or variables include blood flow velocity and velocity profile characteristics. The detection of stagnant or recirculating flow regions can relate to propensity of cell adhesion to the endothelium, whereas the detection of slightly turbulent flow can indicate a stenosis that could be angiographically silent. In addition, the levels of shear force can be important for detecting disease-prone regions or shear-induced platelet activation. There are other hemodynamic variables, such as local pressure gradient, that can also be measured or derived from measurements by a sensor such as an optical fiber sensor with the intent of identifying regions at high risk for clinical complication.

Additional sensors disposed within the guidewire 10, such as optical fiber sensors, can be capable of measuring temperature, pressure, flow, velocity, turbulence, shear stress, etc., of a treatment site. A physician can then use this information in making treatment decisions. For example, if the additional sensor identifies flow discontinuities or abnormal flow rates and the guidewire 10 can be operatively coupled to a balloon catheter, the physician can use this information to optimize an angioplasty. Or, if the additional sensor is disposed within the guidewire 10 that is used as a stent delivery system, the physician can use the information to optimize the dilatation of the stent.

Method of Use

In one method of using the present invention, a medical professional (e.g. cardiologist) inserts the guidewire 10 into the patient's vasculature and advances it to a specified location in the vasculature. The sensor 12 can be selected based on the sensor's capability of detecting the particular physical characteristic or variable, be it NO, superoxide, presence of other molecules containing oxygen, etc. Once the guidewire 10 is in place, the data system 62 can be operated to send and receive signals. The received signals are processed by the data system 62 to provide information on a display such that the medical professional can view this information and determine how to proceed.

The medical professional can choose to perform a therapeutic procedure, such as balloon angioplasty or stenting, or decide that further treatment is not required. The medical professional can also decide that further information on that section of the vasculature is necessary and either continue with the same guidewire-based sensor or use a different sensor to try to obtain different physical characteristics or data.

A catheter can be operatively fitted over the guidewire 10 (although fitting can occur before entry of the guidewire into the patient) and the catheter can be fed to a desired length along the guidewire. The guidewire 10 can be completely or partially removed from the patient, leaving the catheter in place in the patient. Because the inventive guidewire provides data of the conditions at the end of the catheter, the medical professional can choose to leave the guidewire in place within the patient while the catheter is also in place within the patient.

One way to amplify biological NO response can be to administer a pharmacological stimulant such as acetylcholine to increase NO production. With the guidewire 10 in place, the pharmacological stimulant could be delivered through a catheter with a lumen, through an opening in the guidewire 10, or through any device with drug delivery capacity. The amplified NO response can be helpful to improve NO detection and allow measurements further away from the tissue to be analyzed. Levels of NO in stimulated, diseased tissue also can provide additional data points for diagnostic analysis (in addition to the baseline, unstimulated NO levels). These two sets of data points can provide diagnostic information when compared against each other and when compared to stimulated and unstimulated NO levels for healthy tissue.

The guidewire 10 of the present invention provides several advantages over the relatively few current diagnostic and therapeutic devices used in the art. The guidewire 10 can sense extremely small gradients of relevant chemical parameters throughout the human vascular system and in the critical areas surrounding the treatment site to provide more comprehensive information on the disease state. A catheter need not be used to make the guidewire functional. The guidewire can be used by itself to gather NO and/or superoxide and/or supplemental readings because of the functional sensor.

Although the invention has been disclosed in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

We claim:

1. A method for performing a therapeutic procedure, comprising:
    providing a guidewire having an outside diameter, comprising:
        an elongated member including a lumen disposed along a segment of the elongated member and an opening positioned so that the lumen is in fluid communication with the vessel,
        a shaping ribbon having a distal and proximal end, the distal end secured to a rounded tip and the proximal end secured to a distal end of the elongated member, and
        a sensor positioned within the lumen so that the sensor is in fluid communication with the vessel through the opening, the sensor being capable of measuring the level of nitric oxide or superoxide in the vessel,
        wherein the sensor is capable of being moved independently of the distal end of the elongated member;
    providing a treatment catheter including a lumen having an inside diameter larger than the outside diameter to enable sliding of the treatment catheter over and along the guidewire;
    positioning the guidewire at a specified location within a vessel;
    allowing a body fluid to enter the lumen through the opening in the elongated member of the guidewire so that the body fluid is in contact with the sensor;
    measuring the level of nitric oxide or superoxide of the body fluid in contact with the sensor; and
    based on the measured level of nitric oxide or superoxide, performing the therapeutic procedure including the step of guiding a treatment catheter to the specified location by sliding the treatment catheter over and along the guidewire.

2. The method of claim 1, wherein the vessel is a blood vessel.

3. The method of claim 1, wherein the measuring step includes delivering, using the guidewire, a stimulant to amplify a biological nitric oxide or superoxide response to improve nitric oxide or superoxide detection by the sensor.

4. The method of claim 3, wherein the stimulant comprises acetylcho line.

5. The method of claim 1, wherein the designated region within the vessel is affected by thrombosis or restenosis.

6. The method of claim 1, further comprising bending the sensor away from a central longitudinal axis of the distal end of the elongated member in order to measure the level of nitric oxide or superoxide of the body.

7. The method of claim 1, further comprising sliding the sensor along the distal end of the elongated member in order to measure the level of nitric oxide or superoxide of the body.

8. The method of claim 7, further comprising rotating the sensor.

9. The method of claim 1, wherein the performing the therapeutic procedure includes the step of selecting angioplasty or stenting based on the measured levels of nitric oxide or superoxide.

10. The method of claim 1, wherein the guidewire includes a flexible coil having a helical configuration displaced around the distal end of the elongated member.

11. A method for performing a therapeutic procedure, comprising:
    providing an guidewire having an outside diameter, comprising:

an elongated member including a lumen disposed along a segment of the elongated member, a sensor positioned within the lumen of the elongated member so that the sensor is in fluid communication with the vessel, the sensor being capable of measuring the level of nitric oxide or superoxide in the body fluid, wherein the sensor is capable of being moved independently of a distal end of the elongated member; and a shaping ribbon having a distal and proximal end, the distal end secured to a rounded tip and the proximal end secured to the distal end of the elongated member;

providing a treatment catheter including a lumen having an inside diameter larger than the outside diameter to enable sliding of the treatment catheter over and along the guidewire;

positioning the guidewire at a specified location within a vessel;

allowing a body fluid to make contact with the sensor;

measuring the level of nitric oxide or superoxide of the body fluid in contact with the sensor at the specified location; and based on the measured level of nitric oxide or superoxide, performing the therapeutic procedure including the step of guiding a treatment catheter to the specified location sliding the treatment catheter over and along the guidewire.

12. The method of claim 11, wherein the vessel is a blood vessel.

13. The method of claim 11, wherein the designated region within the vessel is affected by thrombosis or restenosis.

14. The method of claim 11, additionally including delivering a stimulant to increase the production of nitric oxide or superoxide.

15. The method of claim 14, wherein the stimulant comprises acetylcholine.

16. The method of claim 11, further comprising bending the sensor away from a central longitudinal axis of the distal end of the elongated member in order to measure the level of nitric oxide or superoxide of the body.

17. The method of claim 11, further comprising sliding the sensor along the distal end of the elongated member in order to measure the level of nitric oxide or superoxide of the body.

18. The method of claim 17, further comprising rotating the sensor.

19. The method of claim 11, wherein the performing the therapeutic procedure includes the step of selecting angioplasty or stenting based on the measured levels of nitric oxide or superoxide.

20. The method of claim 11, wherein the measuring step includes delivering, using the guidewire, a stimulant to amplify a biological nitric oxide or superoxide response to improve nitric oxide or superoxide detection by the sensor.

21. The method of claim 20, wherein the stimulant comprises acetylcho line.

22. The method of claim 11, wherein the guidewire includes a flexible coil having a helical configuration displaced around the distal end of the elongated member.

23. A method for performing a therapeutic procedure, comprising:

providing a guidewire having an outside diameter, comprising:

an elongated member including a lumen disposed along a segment of the elongated member, a tapered distal core section forming an opening, and a helical coil or polymeric jacket attached at a proximal end thereof to the distal core section and at a distal, rounded tip of the guidewire to a ribbon cable, a sensor positioned within the lumen of the elongated member so that the sensor is in fluid communication with the vessel through the opening, the sensor being capable of measuring the level of nitric oxide or superoxide in the vessel, wherein a tip of the sensor is disposable within the rounded tip when the guidewire is being advanced to the specified location within a vessel, and wherein the sensor is capable of being moved independently of the distal core section;

providing a treatment catheter including a lumen having an inside diameter larger than the outside diameter to enable sliding of the treatment catheter over and along the guidewire;

positioning the guidewire at a specified location within a vessel;

allowing a body fluid to enter the lumen through the opening in the elongated member of the guidewire so that the body fluid is in contact with the sensor;

measuring the level of nitric oxide or superoxide of the body fluid in contact with the sensor; and based on the measured level of nitric oxide or superoxide, performing the therapeutic procedure including the step of guiding a treatment catheter to the specified location by sliding the treatment catheter over and along the guidewire.

24. A method for performing a therapeutic procedure, comprising:

providing an elongated guidewire having an outside diameter, comprising:

an elongated member including a lumen disposed along a segment of the elongated member, a tapered distal core section forming an opening, and a helical coil or polymeric jacket attached at a proximal end thereof to the distal core section and at a distal, rounded tip of the guidewire to a ribbon cable, a sensor positioned within the lumen, the sensor being capable of measuring the level of nitric oxide or superoxide in the body fluid, wherein the sensor is capable of being moved independently of the distal core section, and wherein a tip of the sensor is disposable within the rounded tip when the guidewire is being advanced to the specified location within a vessel;

providing a treatment catheter including a lumen having an inside diameter larger than the outside diameter to enable sliding of the treatment catheter over and along the guidewire;

positioning the guidewire at a specified location within a vessel;

allowing a body fluid to make contact with the sensor;

measuring the level of nitric oxide or superoxide of the body fluid in contact with the sensor at the specified location; and based on the measured level of nitric oxide or superoxide, performing the therapeutic procedure including the step of guiding a treatment catheter to the specified location sliding the treatment catheter over and along the guidewire.

* * * * *